United States Patent [19]

Smith et al.

[11] Patent Number: 4,460,336

[45] Date of Patent: Jul. 17, 1984

[54] ORTHODONTIC ATTACHMENTS

[76] Inventors: Dennis C. Smith, 183 St. Clair Ave. E., Toronto, Ontario; Rolf Maijer, 435 Trunk Rd., Ste. 207, Duncan, British Columbia, both of Canada

[21] Appl. No.: 402,307

[22] Filed: Jul. 27, 1982

[51] Int. Cl.³ .............................................. A61C 7/00
[52] U.S. Cl. ........................................................ 433/9
[58] Field of Search ................................... 433/9, 228

[56] References Cited

U.S. PATENT DOCUMENTS

| | | | |
|---|---|---|---|
| 3,775,850 | 12/1973 | Northcutt | 433/9 |
| 4,068,379 | 1/1978 | Millar et al. | 433/9 |
| 4,180,911 | 1/1980 | Bullock | 433/9 |
| 4,244,689 | 1/1981 | Ashman | 433/201 |
| 4,351,069 | 9/1982 | Ballintyn | 433/201 |

*Primary Examiner*—Robert Peshock
*Attorney, Agent, or Firm*—Sim & McBurney

[57] ABSTRACT

Orthodontic brackets or other dental attachments are provided with particulate material on the tooth engaging surface thereof to improve the bonding of bracket to a tooth surface.

The particulate material consists of metal spheres joined to each other and to the tooth engaging surface at their points of contact therewith.

4 Claims, No Drawings

ORTHODONTIC ATTACHMENTS

FIELD OF INVENTION

The present invention relates to novel orthodontic and other dental attachments, such as, brackets, bases, bands, periodontal splints and oral-surgical splints.

BACKGROUND TO THE INVENTION

In orthodontic surgical procedures, orthodontic brackets commonly are attached directly to teeth by adhesive bonding. The tooth surface often is acid etched, so that a micro-mechanical interlock is achieved between the resin and the etched surface. Alternatively, as described in our copending U.S. patent application Ser. No. 235,166, the disclosure of which is incorporated herein by reference, the surface of the tooth may be provided with a crystal growth to which the resin is bonded.

There is also a mechanical bond between the bracket base abutting the tooth and the resin. This mechanical bond represents the weak point of the assembly and brackets can become detached from the teeth by failure of the mechanical bond at the bracket/resin interface, if the shear strength thereof is exceeded. A variety of base designs have been proposed and utilized in an attempt to overcome this problem. Some examples include a stainless steel base with perforations, a stainless steel mesh base, a foil mesh base with a thin piece of stainless steel welded to a mesh backing, a metal base with machined retentive undercuts, plastic brackets and bases constructed of polycarbonate, and ceramic bases and brackets.

Although these bracket designs provide reasonably good bonding, there are a number of practical disadvantages associated with the designs. For example, perforated stainless steel bases may produce staining around the perforations at the adhesive level. In welded brackets, weld spots may obliterate the retentive areas in mesh bases, leading to decreased bond strength, and weld spots at the edges of the base may lead to leakage and corrosion. Plastic bases are difficult to bond to with current resin bonding systems while ceramic bases are bulky and may show brittle characteristics.

SUMMARY OF INVENTION

In accordance with the present invention, there is provided a novel structure of dental attachment which overcomes the problems of the prior art structures and has several advantages when compared with the prior art stuctures.

The present invention provides a dental attachment, including brackets, bases, bands, periodontal splints and oral surgical splints, which has the tooth engaging surface thereof provided with an adherent particulate coating.

The provision of the particulate coating on the tooth engaging surface thereof enables improved bonding between the tooth and the dental attachment to be achieved, without the problems attendant the prior art structures.

GENERAL DESCRIPTION OF INVENTION

The particulate coating may be formed on the tooth engaging surface of the attachment in any convenient manner, such as, by fusion or by sintering. The particles making up the coating may be any convenient shape, including a spherical shape or an irregular shape, and may be constructed of metal (including alloys), ceramic, polymer, or a mixture of materials.

The material of construction of the particles usually, but not necessarily, is the same as the material of construction of the substrate, in which case the particles usually are bonded to the substrate through their material of construction. An example of a structure according to the invention wherein dissimilar materials are used is a porous coating of ceramic material on a stainless steel or other metal substrate.

The particulate coating adhered to the tooth engaging surface may take the form of discrete particles which are spaced apart from each other on the surface, or the form of a layer or multiple layers of particles bonded together to produce a network of interconnected pores.

The particulate coating provides a porous interface into which a fluid bonding resin may readily flow and penetrate. Upon curing of the resin to solid form, mechanical interlock is achieved between the cured resin and the particulate coating.

Under some circumstances chemical bonding in addition to this mechanical bonding may be achieved, for example, by the use of polycarboxylate or glass ionomer cements with stainless steel and other metallic substrates and with ceramic substrates.

The thickness of the particulate coating on the tooth engaging surface of the dental attachment in this invention may vary widely depending on the size of the particles and the number of layers desired in the coating. The thickness of the particulate coating generally is up to about 500 micrometers, preferably about 50 to about 300 micrometers.

For a coating comprising discrete particles, irregular particles or spherical particles of about 20 to about 100 microns in diameter with a spacing of about 20 to about 300 microns between them are preferred.

For a coating of integrally-joined particles which make up a porous structure having a plurality of interconnected pores extending therethrough, the particles are usually about $-100$ mesh and preferably a mixture of particles of varying particle sizes restricted to one of three size ranges, namely $-100 +325$ mesh (about 50 to about 200 microns), $-325 +500$ mesh (about 20 to about 50 microns) and $-500$ mesh (less than about 20 microns).

The size of the particles in the porous structure determines the pore size of the pores between the particles. Smaller-sized pores are preferred for fluid resin bonding agents whereas larger-sized pores are preferred for more viscous cementitious bonding materials. The selection of particle size is also used to control the porosity of the coating to within the range of about 10 to about 50% by volume.

An adequate structural strength is required for the composite of substrate and coating, so that any fracture of the joint of the bracket to the tooth occurs in the resin and not in the coating. To achieve this condition, the structural strength of the coating, the interface between the coating and the substrate and the substrate itself is at least 8 MPa.

One embodiment of the invention is an orthodontic bracket constructed of stainless steel or other suitable metal or alloy, and which has the tooth engaging surface of the base provided with a porous coating. The bracket base may vary in size from about 3 mm in diameter to an area of about 4×8 mm, according to the type of attachment required.

If desired, a continuous strip of stainless steel or other alloy of about 5 to 10 mm wide may be coated with particles. Such strip then may be used to construct the base bonding surface of the orthodontic brackets or other attachments, or may be used to form orthodontic bands. When the invention takes the form of orthodontic bands, these may be preformed and then coated on the interior with the particles to provide the bonding surface.

As mentioned above, when the tooth-engaging surface and coating are metal, the coating may be formed by sintering or by fusion. When particles of other materials, such as, ceramics or polymers, are applied to metallic substrates or substrates of other materials, such as, ceramic or polymer, then any convenient technique known in the coating art may be used to produce the coated substrate.

EXAMPLES

EXAMPLE 1

Commercial stainless steel orthodontic bracket bases were coated with a slurry of stainless steel beads having diameters in the range of 44 to 180 micrometers and the coated bases were sintered in a vacuum furnace at a temperature of about 1400° C. A porous coated base resulted in which the porous coating had a thickness of 0.5 mm and a porosity of about 40% by volume.

When the bases were bonded to acid etched surfaces of human teeth using Orthomite 11 bracket bonding resin (Rocky Mountain Dental Products, Denver, Colo.), the bond strength of the resulting joint was found to be 11.9 kg, compared with 7 kg for brackets having a perforated base.

EXAMPLE 2

A series of commercial stainless steel orthodontic bracket bases was modified by powder coating with cobalt-chromium alloy beads of less than 100 mesh in diameter to produce coatings of 0.5 to 0.7 mm thickness. After bonding to bovine teeth, the bond strength was determined in each case. The results are set forth in the following Table I and are compared with those from a conventional mesh base bracket bonded under the same conditions:

TABLE I

| Sample | Average Bond Strength $Kg/cm^2$ |
| --- | --- |
| Mesh base | 66.5 |
| −100 + 325 mesh beads | 154.8 |
| −325 mesh beads | 125.8 |

EXAMPLE 3

A glass ceramic powder with an average particle size of 40 microns was chemically bonded to a commercial stainless steel orthodontic bracket base. The brackets were bonded to acid etched bovine enamel using Solo-tack orthodontic bonding resin (L. D. Caulk Co, Milford, Del.). The average tensile bond strength after 24 hours conditioning in water at 37° C. was found to be 59 $Kg/cm^2$.

SUMMARY OF DISCLOSURE

In summary of this disclosure, the present invention provides novel orthodontic and other dental attachments which achieve superior bonding to teeth as compared with the prior art. Modifications are possible within the scope of this invention.

What we claim is:

1. An orthodontic bracket comprising an attachment base for the adhesion of said bracket to a tooth and having a tooth engaging surface varying in size from about 3 mm in diameter to an area of about 4×8 mm, and a porous coating on said tooth engaging surface consisting of metal spheres joined to each other and to said tooth engaging surface at their points of contact therewith, said porous coating having a thickness of about 50 to about 300 microns and a porosity of about 10 to about 50 volume %, spheres having a particle size of −100 mesh, and said porous coating, the interface between said porous coating and said tooth engaging surface and said tooth engaging surface having a structural strength of at least 8 MPa.

2. The bracket of claim 1 wherein said metal spheres have a particle size of −300 mesh.

3. The bracket of claim 1 wherein said metal spheres have a particle size of −500 mesh.

4. The bracket of claim 1, 2 or 3 constructed of stainless steel.

* * * * *